United States Patent [19]

Lynn et al.

[11] Patent Number: 5,178,607
[45] Date of Patent: Jan. 12, 1993

[54] BLOOD ASPIRATION ASSEMBLY SEPTUM AND BLUNT NEEDLE ASPIRATOR

[76] Inventors: Lawrence A. Lynn, 862 Curleys Ct., Worthington, Ohio 43085; James E. Cole, 891 Via Arroyo, Ventura, Calif. 93003

[21] Appl. No.: 594,677

[22] Filed: Oct. 10, 1990

Related U.S. Application Data

[60] Division of Ser. No. 302,835, Jan. 27, 1989, abandoned, which is a continuation-in-part of Ser. No. 80,406, Jul. 31, 1987, Pat. No. 4,838,855.

[51] Int. Cl.⁵ .............................................. A61M 37/00
[52] U.S. Cl. ...................................... 604/86; 604/122; 604/244; 128/762
[58] Field of Search ............... 604/4, 35, 36, 38, 83, 604/86, 87, 88, 91, 117, 122, 201, 239, 244, 256, 905; 128/673, 760, 762-766

[56] References Cited

U.S. PATENT DOCUMENTS

| | | |
|---|---|---|
| 2,922,420 | 1/1960 | Cheng .................................. 604/272 |
| 3,067,742 | 12/1962 | Linke et al. ........................ 604/414 |
| 3,406,685 | 10/1968 | May ..................................... 604/170 |
| 4,014,328 | 3/1977 | Cluff et al. ......................... 128/760 |
| 4,058,121 | 11/1977 | Choksi et al. ...................... 604/274 |
| 4,197,848 | 4/1980 | Garrett et al. ....................... 604/19 |
| 4,276,880 | 7/1981 | Malim .................................. 604/264 |
| 4,496,350 | 1/1985 | Cosentino .............................. 604/4 |
| 4,645,491 | 2/1987 | Evans ................................... 604/158 |
| 4,650,468 | 3/1987 | Jennings ............................. 604/110 |
| 4,654,034 | 3/1987 | Masters et al. ...................... 604/192 |
| 4,666,438 | 5/1987 | Raulerson ........................... 604/272 |
| 4,675,004 | 6/1987 | Hadford et al. ...................... 604/44 |
| 4,675,005 | 6/1987 | De Luccia .......................... 604/110 |
| 4,675,007 | 6/1987 | Terry .................................. 604/283 |
| 4,675,017 | 6/1987 | Sato .................................... 604/405 |
| 4,699,612 | 10/1987 | Hamacher ............................. 604/51 |
| 4,710,180 | 12/1987 | Johnson .............................. 604/239 |
| 4,721,506 | 1/1988 | Teves .................................... 604/51 |
| 4,763,648 | 8/1988 | Wyatt .................................. 604/201 |
| 4,776,843 | 10/1988 | Martinez et al. ..................... 604/86 |
| 4,834,152 | 5/1989 | Howson et al. ..................... 604/414 |
| 4,838,877 | 6/1989 | Massau ............................... 604/272 |
| 4,865,583 | 9/1989 | Tu ........................................ 604/86 |
| 4,911,705 | 3/1990 | Heinzerling et al. ............... 604/201 |

FOREIGN PATENT DOCUMENTS 2049513 3/1971 France ................................. 604/88

OTHER PUBLICATIONS

Catalog American Scientific Products p. 1568 1987-1988.

Primary Examiner—John D. Yasko
Assistant Examiner—Anthony Gutowski
Attorney, Agent, or Firm—Cushman, Darby & Cushman

[57] ABSTRACT

A blood aspiration assembly has an aspirator receiver. The receiver has a housing with a rigid casing and a resilient plug, and a liquid flow chamber. The chamber has an offset lower wall surface, to create turbulence to remove air bubbles during initial set up. The offset wall can be elevated with an intermediate part of larger cross section to accommodate the blunt needle. The plug has a slit or perforation to allow passage of a blunt needle therethrough. The plug can have two parts of different compliance, with aligned slits or perforations. The blunt needle tip can be rounded or flat, with a side opening for the needle bore. The contour of the needle tip and the design of the plug are correlated such that the working force required to penetrate the needle tip into the plug perforation is considerably less than the force required for said needle tip to penetrate normal intact human skin of the hands or arms. A stop prevents the needle from contacting the aspiration chamber wall.

35 Claims, 4 Drawing Sheets

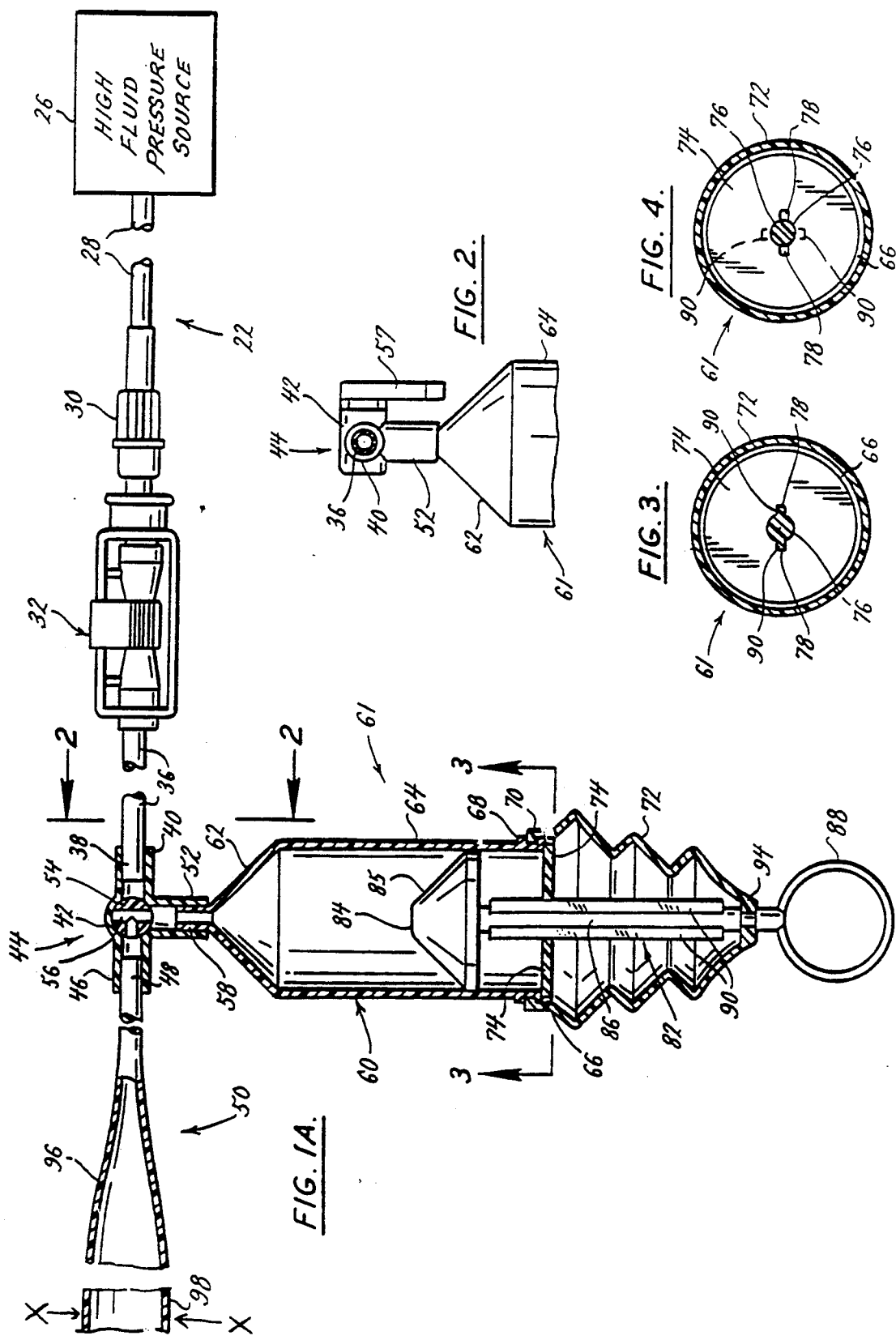

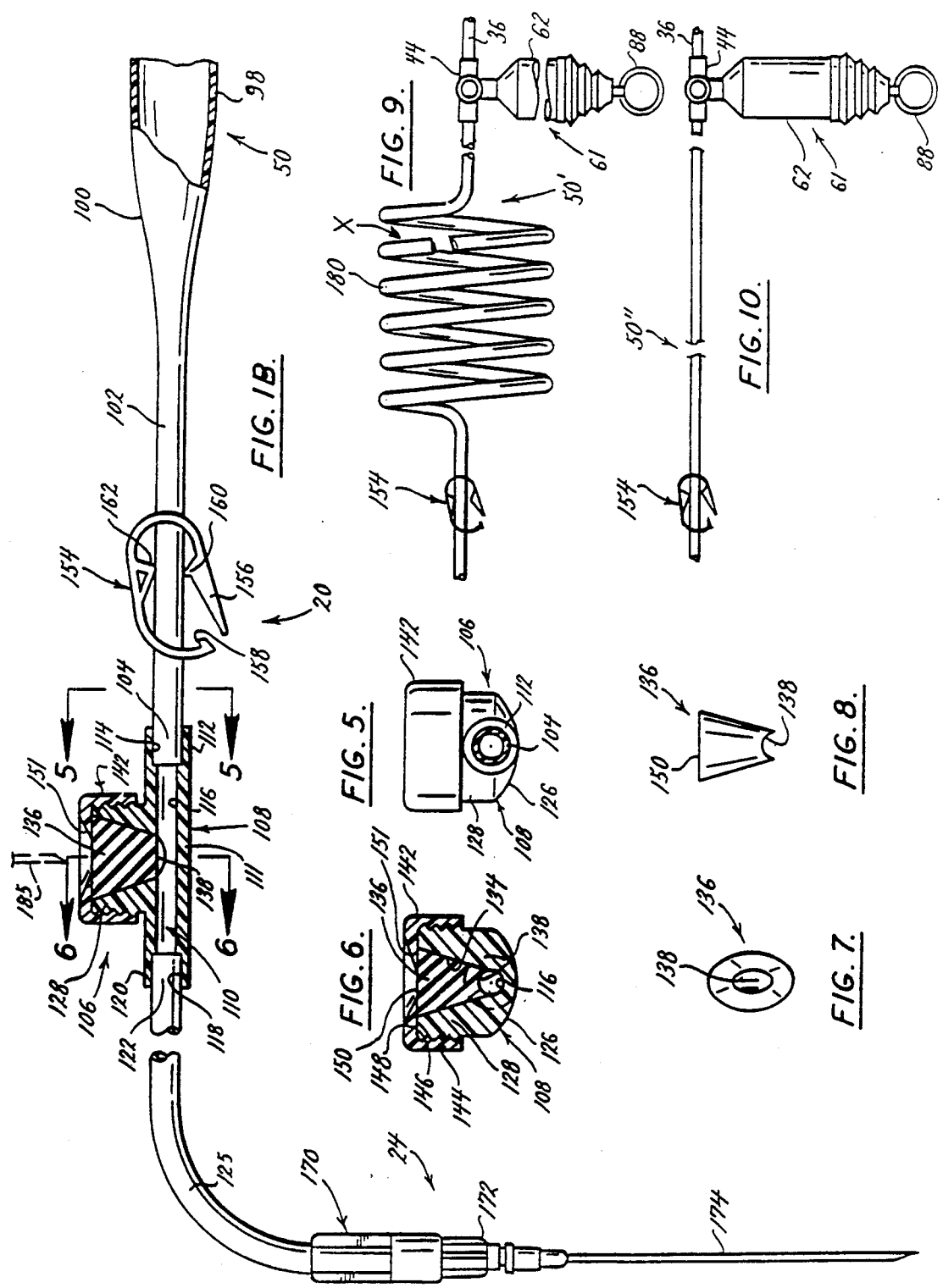

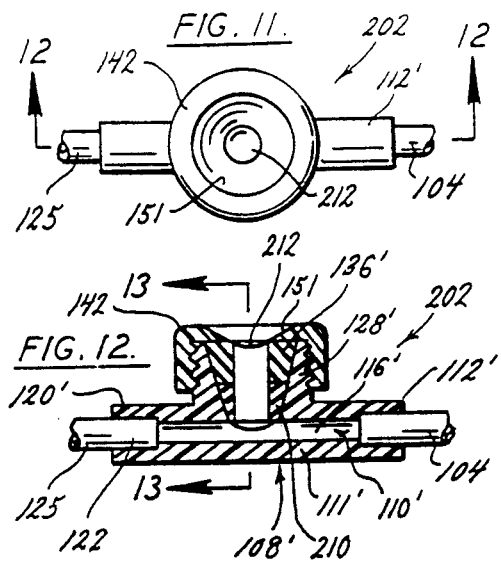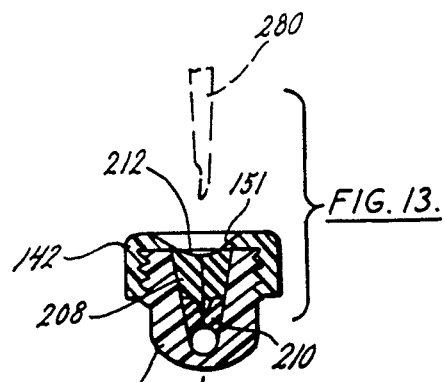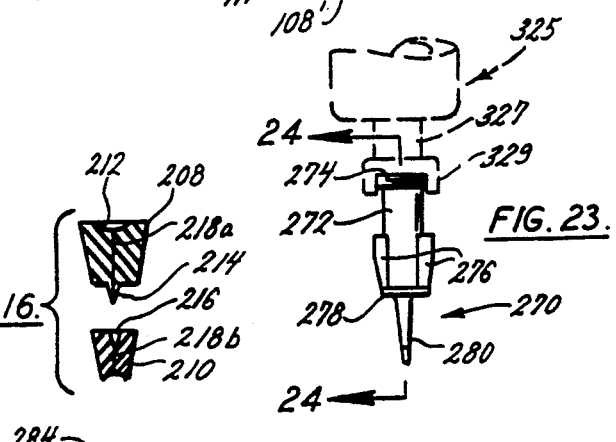

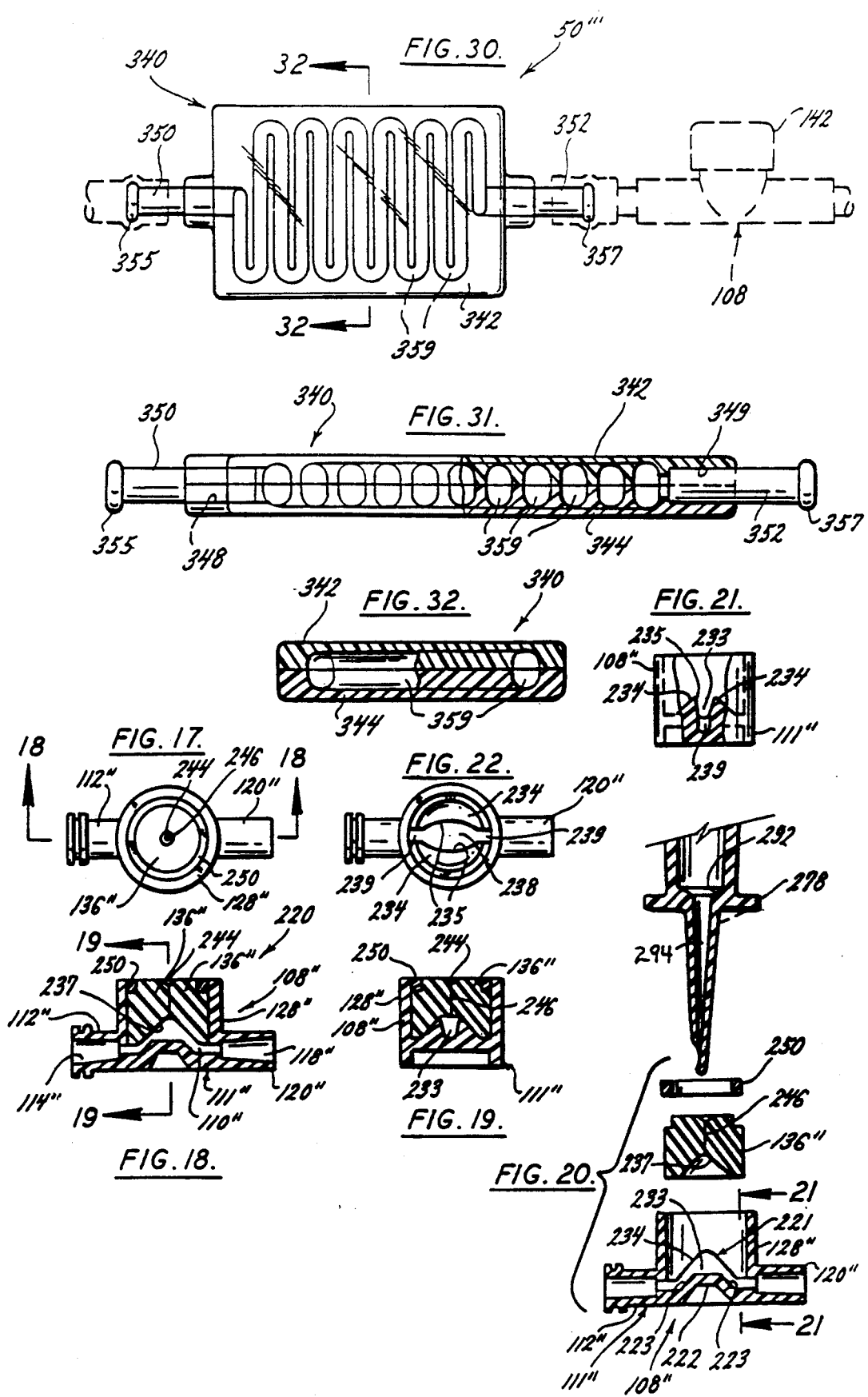

BLOOD ASPIRATION ASSEMBLY SEPTUM AND BLUNT NEEDLE ASPIRATOR

This application is a division of application Ser. No. 07/302,835, filed Jan. 27, 1989, (abandoned) which is a continuation-in-part of application Ser. No. 07/080,406 filed Jul. 31, 1987 (now U.S. Pat. No. 4,838,855.)

BACKGROUND AND SUMMARY OF THE INVENTION

This invention relates to human blood aspiration assemblies and methods of their use. It is necessary and indeed critical to frequently draw blood from patients having a broad variety of illnesses. Cumulative and repetitive blood sampling must be conducted in a number of instances. Such blood samples are often drawn through tubing systems that are connected to indwelling catheters to avoid the pain, inconvenience and potential complications of frequent penetration of the patient's skin.

These tubing systems are often maintained in near-constant direct fluid communication with the vasculature through the catheter, and are used for monitoring pressures within the vasculature, for fluid administration, or simply for maintaining a channel for easy access to the vascular system.

These tubing systems generally contain an electrolyte or dextrose solution when in fluid connection with the vasculature. The reflux of blood into such tubing systems is prevented by maintaining fluid pressure within such tubing equal to, or higher than, that in the vessel in which the catheter dwells. This pressure avoids thrombotic occlusion of the tubing system or catheter while allowing the system to remain patent, or unobstructed despite near constant fluid communication with the vascular system.

In the prior art, such an above-described system can have a proximal tubing segment portion which is closest to the high pressure source, a distal tubing segment which is closer to the catheter, and a channel which opens to the atmosphere (atmospheric channel). This channel is usually capped. A three-way stopcock is connected to the channel and is in line with the tubing. Normally the stopcock connects the proximal tubing to the distal tubing, with the atmospheric channel closed.

When a blood sample is desired, the cap covering the atmospheric channel is removed. A separate syringe is moved by the hand and its neck connected to the atmospheric channel. The stopcock is then turned to open the distal tubing to the syringe. This places the vascular system in direct fluid communication with the syringe. Fluid can then be aspirated from the tubing and the vascular system into the syringe. Upon aspiration, the initial liquid entering the syringe is the resident fluid in the distal tubing segment.

After this, blood, diluted with such resident fluid, will enter the syringe. Finally, after all the resident fluid has been aspirated into the syringe, undiluted blood will enter the syringe and will entirely fill the distal tubing. The stopcock is then closed to the atmospheric channel, and the first syringe is detached from the stopcock. The first syringe is in many uses discarded. With premature infants or small babies, the diluted blood in the first syringe may be reinjected after the blood sample for testing is obtained. But there is a risk of clot formation, thrombosis or infection when this attempt to save blood is made.

A second syringe then must be attached to the atmospheric channel and the stopcock is reopened to the second syringe to thereby place the syringe in fluid communication with the distal tubing that is filled with undiluted blood.

Undiluted blood is then aspirated into the second syringe from the distal tubing and the vasculature in the amount desired for analysis. When sufficient blood is obtained, the stopcock is closed to the second syringe. The second syringe is removed. At this point in some cases, to save blood, the diluted blood is reinjected from the first syringe back into the stopcock with the aforesaid hazards of thrombosis, clotting and infection. The stopcock is thence commonly closed to the distal tubing and opened to produce liquid communication between the proximal tubing and the atmospheric channel.

Following this, the pressure in the more proximal tubing is increased to allow fluid to escape from the proximal tubing out the atmospheric channel to clear residual blood from this channel. Next, the cap is replaced over the atmospheric channel. The stopcock is then closed to the atmospheric channel and opened to the distal tubing segment to reestablish the original fluid communication between the proximal and distal tubing. Following this, the pressure is again increased in the proximal tubing so that fluid will enter the distal tubing from the proximal tubing, thereby forcing the fluid within the distal tubing back into the vascular system through the catheter. As a result, the tubing system again becomes entirely filled with electrolyte or dextrose solution.

Several problems exist in the prior art. First, the procedure often requires the initial sample of blood (which is obtained to clear the resident fluid from the tubing) to be discarded, since it is diluted by the withdrawal procedure. This results in a loss of blood from the patient which is cumulative over many sample aspirations. Eventually, this can produce anemia and could necessitate a blood transfusion to replace such cumulative blood losses. (See "Phlebotomy For Diagnostic Laboratory Tests In Adults, Pattern Of Use and Effect On Transfusion Requirements", *New England Journal Of Medicine*, Vol. 31, p. 1233, 1986; and "Medical Vampires" (Editorial), *New England Journal Of Medicine*, Vol. 31, p. 1250, 1986).

Patients who require many blood samples to be taken during protracted illnesses or after severe trauma may require transfusions which would not otherwise be necessary, and may therefore be subject to the increased risk of blood transfusion related infectious diseases such as hepatitis and A.I.D.S., for example.

Moreover, the stopcock in conventional systems must frequently be open to a channel which is intermittently exposed to the atmosphere. Hence, there is a significant risk of microorganisms contaminating the stopcock and thereby entering the vascular system producing infections which may be extremely serious and even fatal. (See "Stopcock: Bacterial Contamination and Invasive Monitoring Systems", *Heart & Lung*, Vol. 8, p. 100, 1979; and "Stopcock Contamination In An ICU", *American Journal of Nursing*, Vol. 75, p. 96, 1975).

An additional problem is the potential for dilutional error introduced into the blood samples obtained. This results when hospital personnel fail to remove enough blood to adequately clear the resident fluid from the indwelling catheter and its connected tubing. This has been reported in the medical literature to cause error in both measured blood gas values and hematocrit concentrations. Such erroneous hematocrit values have been noted as a potential source of unnecessary blood transfusions in surgical patients. It has been noted that the first syringe must withdraw a volume of intravenous solution and blood that is six times the volume of the tubing distal to the stopcock. (See "Errors In Intraoperative Hematocrit Determination", *Anesthesiology*, Vol. 45, p. 357, 1976; and "Effect of Sample Dilutions on Arterial Blood Gas Determinations", *Critical Care Medicine*, Vol. 13, p. 1067, 1985).

Furthermore, many present conduit systems provide internal diameters which vary abruptly over the length of the conduit. The abrupt change in diameters results in areas where fluid flow is not streamlined, and where pockets of fluid can gather while the main fluid flow goes onward. Accordingly, when blood is drawn into the system from the catheter to displace the resident fluid, pockets of residual resident fluid may remain within the conduit channel. This can dilute any aspirated blood samples later drawn.

Another shortcoming is that the present method of obtaining undiluted blood samples from fluid-filled tubing connected with the vascular system is cumbersome and inconvenient.

With regard to the needle apparatus and special aspirator plug aspect of the invention, the risk of accidental needle puncture has been well known for a long time, and for more than a decade has been known as a common cause of infection of hospital personnel with hepatitis virus. Such needle punctures now are accompanied by the risk of infection with the AIDS virus. The risk of needle puncture is especially acute during the time when needles are inserted into a fluid-filled tubing that is connected to an indwelling vascular catheter to obtain a blood sample. Tubing systems heretofore used have often included septums for blood sampling or medication injection. These septae are designed to be punctured by sharp needles to allow entry of the needle into the tubing so that the needle tip is in fluid communication with the liquid within the tubing.

Such insertion of the needle into the tubing allows a blood sample to be aspirated from the tubing, or allows injection of medication into the tubing. The needles used to penetrate these septae are sharp and can easily penetrate human skin with even casual inadvertent contact. In addition, misdirection of the needle tip against the skin with the same force required to penetrate into the septum will invariably cause skin puncture accompanied by the risk of a fatal or extremely hazardous infection.

Hence, there has long been a need to solve the problem of accidental needle sticks associated with penetrating a septae in order to withdraw blood or inject medication.

SUMMARY OF THE INVENTION

The present invention has features which improve over the art. The present invention allows aspiration of undiluted blood samples from tubing connected to arterial catheters without opening the tubing system to the atmosphere. With the present invention, there is no need to discard an initial blood sample. Hence, this invention eliminates the loss of blood samples through discard and reduces the potential for the introduction of microorganisms into the vasculature.

The features of the invention additionally reduce the exposure of hospital personnel to blood products, and hence reduces exposure of such personnel to contraction of diseases carried by blood products. With use of the present invention, there will be a reduction in the number of transfusions, especially in neonates and patients with protracted critical illnesses.

The invention may significantly reduce the incidence of nosocomial bacteremia and the associated morbidity and mortality caused by the introduction of microorganisms into tubing through conventional stopcocks. Moreover, the present invention simplifies the procedure. The invention reduces the potential for measurement error introduced by the dilution of the blood samples obtained.

An embodiment of the invention comprises proximal, intermediate and distal tubing sections. The proximal section can be in fluid flow connection with a source of higher fluid pressure. Such source can be a liquid-filled container of intravenous fluid such as dextrose or electrolyte, which is elevated or surrounded by a source of increased pressure, for example, a pressure bag. The proximal tubing section extends to a two-way valve. The two-way valve is further connected to the intermediate tubing section. The intermediate tubing is connected to an aspirator receiver. The aspirator receiver is in turn connected to the distal tubing. The distal tube connects to an indwelling catheter.

In one position, the valve connects the intermediate tubing with a reservoir. In the other position, the valve connects the intermediate tubing with the proximal tubing and hence with the aspirator receiver and the distal tubing.

A clamp or valve can be placed with the intermediate tubing to either block or permit liquid flow therethrough.

The aspirator receiver can comprise a housing in liquid communication with the intermediate and distal tubes. The housing has a portion comprising a resilient material, such as silicone. In an embodiment, part of the housing can be of rigid material which comprises a casing, and the resilient material can fit within a bore of the casing. The housing has a chamber in liquid flow communication with the distal and proximal tubes. The resilient material allows a needle to perforate it so that the needle enters the aspiration chamber. The resilient material automatically seals the perforation produced by the needle when the needle is withdrawn therefrom.

The casing bore can be frustum-shaped. The resilient material can be a plug of conforming shape. In an embodiment, the plug can be of slightly greater diameter than the diameter of the frustum bore so that the plug must be slightly compressed to completely fill the bore when inserted therein. Alternatively, the resilient portion and the casing can be molded together.

The insertion of a needle into the plug will be accommodated by elastic compression of the plug material against the needle. The chamber preferably comprises a cylindrical bore which abuts the plug apex. The plug apex curves to correspond to the curve of the chamber bore to allow smooth liquid flow and prevent trapping of blood or dextrose thereabout.

The reservoir has means for changing pressure within the reservoir, such as a piston which can be locked into both the fully extended intake or discharge positions. When the two-way valve connects the reservoir to the intermediate tube, liquid enters the reservoir from the intermediate tube when the reservoir pressure is below the intermediate tube pressure. Liquid is discharged into the intermediate tubing when the reservoir pressure is greater than the intermediate tube pressure. The intermediate tube can have an enlarged section, or a spiralled section. In either case, the intermediate tube is designed to accommodate substantial volume as will be described below with the linear distance from end to end of the intermediate tube shortened to facilitate handling and operation.

The reservoir has an internal liquid volume potential equal to X. The volume X is also equal to a volume of blood which, when withdrawn from the vasculature through the catheter, through the distal tubing, through the aspirator chamber, and a portion of the intermediate tubing, causes displacement of substantially all the resident fluid from the catheter, the distal tubing, aspiration chamber, and a portion of the intermediate tubing. When the reservoir is filled with volume X of liquid from the intermediate tube, the blood enters the catheter, and the catheter, the distal tubing, and the aspiration chamber, and a portion of the intermediate tubing are thus filled with essentially undiluted blood. Closure of the clamp or valve is preferably on the intermediate tubing at a point so that after the reservoir has been filled with volume X of aspirated liquid from the distal portion of the assembly, the clamp or valve can be closed to isolate a segment of the apparatus distal thereto which contains essentially undiluted blood. Alternatively, the reservoir may be locked in the filled position so that substantial fluid flow cannot occur from the intermediate tubing and the aspiration chamber when the above designated clamp is absent. The predesignated volume X relationship, therefore, provides for consistent and predictable dilution free blood aspiration from the aspirator receiver chamber as will be described below.

When the reservoir is filled and a volume X of fluid has entered the reservoir and a volume X of blood has entered the catheter and apparatus through the distal tip of the catheter, the column of fluid within the assembly comprises three basic segments which progressively merge together a distal segment composed of substantially undiluted blood, an intermediate segment of blood mixed with resident fluid, and a proximal segment of resident fluid which contains essentially no blood. The sum of the internal potential fluid volumes of the catheter, the distal tubing segment, the aspirator receiver chamber, and the intermediate tubing is equal to a volume of Y. The volume Y is greater than the sum of the fluid volumes of the distal segment of essentially undiluted blood and the intermediate segment of blood-resident fluid admixture formed by the above described withdrawal maneuver. Therefore, a proximal portion of the intermediate tubing will contain resident fluid with essentially no blood after the volume X of blood has entered through the catheter into the assembly in response to the withdrawal of the volume X of resident fluid into the reservoir. The volume Y can be considerably larger than the volume X to accommodate variability in the volume of resident fluid which directly mixes with the blood. Thus, blood does not enter the reservoir during such withdrawal. Therefore, the predesignated volume Y relationship provides for prevention of the potential for blood clot formation within the reservoir by preventing blood from entering the reservoir during reservoir filling.

The invention is operated by first opening the two-way valve to connect the reservoir and the intermediate tube. The intermediate tube clamp or valve is open. The reservoir pressure is then reduced to be substantially less than the liquid pressure in the intermediate tube (if that pressure is already not substantially less). A volume of fluid equal to X then enters the reservoir from the intermediate tube. The reservoir then may be locked to maintain the volume X dimensions. A volume of blood equal to X will enter the catheter, distal tube, aspiration chamber, and part of the intermediate tube, as the resident fluid in those parts is displaced proximally through the apparatus, down the pressure gradient generated by the lower reservoir pressure. The intermediate tube clamp or valve is then closed to isolate the blood in the blood aspiration chamber and the part of the apparatus distal thereto, from the blood and liquid proximal to the clamp.

The blood now in the aspiration chamber, the distal tube, and the catheter is virtually undiluted blood. This is because the volume X is predetermined by design to be a volume which virtually completely displaces all resident liquid in juxtaposition with and distal to the aspiration point of the chamber (and distal to the clamp in the intermediate tube if provided) when said volume X is withdrawn into the reservoir as described and replaced by blood entering through an indwelling catheter. A needle connected to a syringe or vacuum-filled container is then inserted through the resilient part of the aspirator receiver until the needle tip enters the blood filled chamber.

Blood is then aspirated into the syringe or container from the chamber with additional blood replacing the aspirated blood through the indwelling catheter. Either the locking of the reservoir fully in the withdrawn position (when the two-way valve connects the reservoir into the intermediate tube) or the closing of the intermediate tube clamp can prevent substantial flow of fluid from the intermediate tube into the aspirator receiver chamber. Both may be provided in the preferred embodiment to reduce the chance of procedural error during operation of the apparatus.

Once a satisfactory sample has been obtained, the syringe needle is withdrawn from the resilient section. The resilient section automatically seals the perforation produced by the needle. The clamp is then opened and the reservoir pressure raised so that the volume X of fluid will re-enter the intermediate tube from the reservoir. This produces a pressure gradient which drives much of the blood which previously entered the apparatus back into the vascular system. The two-way valve is then closed to the reservoir and positioned to place the intermediate and proximal tubes in liquid communication. The pressure in the proximal tube can then be increased if desired, to displace any residual blood from the apparatus into the vasculature.

In a modification, the aspiration chamber can have a flow path to more easily displace air from the chamber when the aspiration assembly is initially installed. It can be desirable to decrease the internal diameter of the tubing extending from the distal side of the aspiration chamber to the patient. However, the aspiration chamber itself must be large enough to accommodate the blunt needle, to be later discussed. Hence, the central portion of the internal flow path of the chamber may be enlarged relative to the distal and proximal portions.

Therefore, a reduction in liquid flow velocity within the enlarged central portion may occur as liquid flows through the central portion of the aspiration chamber. This makes it normally more difficult to remove air bubbles which may collect in the enlarged section within the chamber. In a modified chamber, the flow path through the chamber is designed to create more turbulent flow to increase the ability of the liquid, such as saline solution, to shear away air bubbles adhering to the surface of the chamber walls.

In one specific embodiment, the flow path through the aspiration chamber rises upwardly and thence descends to provide for more flow turbulence. The lower surface of the plug is shaped to accommodate the rise in the chamber flow path.

In a modification, the intermediate tube can comprise a capacitance coil extending in a rectangular rigid casing in a flat plane. The bore can be oblong or elliptical. This design is to achieve maximum volume of the capacitance chamber with minimum topographical surface area. This makes the capacitance casing more easily attachable to a patient. The rigidity of the casing prevents dampening of the pressure waveform within the assembly when it is in fluid connection with a patient's artery. This makes blood pressure readings more reliable.

It is therefore an object of the present invention to provide a method and apparatus of blood aspiration through an indwelling catheter which does not require an initial diluted sample of blood to be collected and wasted (or exposed to a high risk of coagulation or contamination) before the undiluted specimen for analysis is collected.

It is further an object of the invention to provide a method and apparatus of blood aspiration through an indwelling catheter which does not require any channel in fluid connection with the vascular system to be exposed to the atmosphere.

Moreover, an object of the invention is to provide a method and apparatus of blood aspiration which reduces the exposure of hospital personnel to blood products and simplifies the blood aspiration process.

It is yet another object of the invention to provide a method and apparatus of blood aspiration which predictably reduces the risk of measurement error which may be introduced by the dilution of blood samples by fluid from within indwelling catheters or connected tubing.

An additional object of the invention is to provide a channel throughout which flow is substantially unobstructed and hence efficient in displacing resident liquid in the distal channel by blood entering through the catheter. This minimizes the potential for dilution of blood samples by residual pockets of resident liquid within the channel when blood is aspirated. This permits smaller blood samples to be taken with the maintenance of acceptable measurement accuracy.

The invention further solves the problem of accidental needle sticks associated with insertion of a needle through septae in order to withdraw blood from tubing connected to these septae, or to inject medication within that tubing. The invention uses a penetratable plug or septum for use in conjunction with a blood collection or injection device having a blunt needle. The plug is comprised of resilient material having a slit or a perforation extending from its exterior surface to its interior surface which is adjacent the liquid within the tube. The plug can be used with the blood aspiration assembly of the invention.

When a needle is absent from the slit or perforation, the slit or perforation is tightly closed to prevent leakage of fluid from the tubing, such as from the aspiration chamber of the invention, despite high pressure within the tubing system.

The contour of the needle tip and the tightness of the seal of the plug slit or perforation are correlated. This correlation assures that the working force to pass the blunt needle tip into the plug's slit or perforation, is considerably less than the force required to cause the tip of the blunt needle to cause the tip of the blunt needle to penetrate normal intact human skin of the hands or arms.

The presence of the perforation or slit in the plug allows the blunt needle to obtain initial penetration into the plug with a small amount of force. The initial insertion of the blunt needle acts to hold the blunt needle in alignment for further application of force to move the needle tip into the aspiration chamber.

Since the force required to pass the tip of the blunt needle into the septum is considerably less than the force required to penetrate the surface of normal intact human skin of the hand, accidental misdirection of such forces through the needle tip against the skin will not result in penetration. Therefore, the risk of needlestick while obtaining a blood sample through the septum should be virtually eliminated.

The blunt needle has a tip with an enlarged surface area that does not easily pierce the human skin, but which will penetrate the perforated or slitted plug without difficulty. The blunt needle tip can be rounded or flat, with a side opening for the needle bore. The side opening provides a broader distribution of force over the surface area against which application will be made, as opposed to a tip having an orifice extending through its axis against the surface of application.

The roundness of the tip, and the angle of the tip from the rounded portion toward the proximal end of the needle is such to effect penetration of the perforated or slitted plug but reduce the chance of accidental skin puncture. The shape of the needle leading to the tip can be of a generally conical shape to thus provide greater rigidity of the needle, since the initial penetration of the perforated or slitted plug can be achieved by the smaller rounded or flattened tip.

The force required for the blunt needle to penetrate the skin is much greater than that needed for a conventional steel needle to penetrate the skin. As a result, the risk of skin puncture by casual contact with the blunt needle is much less than the risk with the conventional steel needle.

The blunt needle apparatus has a stop, which can be of annular shape, which contacts the aspirator assembly to prevent the tip of the needle from contacting the interior wall of the aspiration chamber. A means for gripping and turning the blunt needle apparatus so that it can be affixed to a syringe, such as projecting flanges, is provided.

In a modification, the plug or septum has an upper part combined with a lower part. The upper part is resilient but is more compliant than the lower part. Both the upper and lower part have either a slit or perforation extending in alignment. This alignment guides the blunt needle inserted through the slit or perforation in the top part into the opening of the slit or perforation in the bottom part. When the blunt needle is inserted through the more pliable first part, the slit or the perforation splints the needle in position to be more stable when the greater force is needed to penetrate the less pliable second part.

The first and second parts of the plug both grip against the needle when the needle tip is inserted to within the aspiration chamber of the tubing. The grip is stronger for the bottom part than for the top part. A tight seal is provided by such gripping to prevent the pressurized liquid within the aspiration chamber or within the tubing, from leaking through the perforation or slit in the plug to pass outside of the upper plug.

The penetratable plug or septum used with a blunt needle greatly improves the elimination of infection and injury caused by accidental needlestick.

DESCRIPTION OF THE DRAWINGS

FIG. 1A shows the proximal part of the assembly, with some parts shown in section, and some parts broken, with a schematic for the high fluid pressure source;

FIG. 1B shows the distal part of the assembly, with some parts shown in section and some parts broken;

FIG. 2 is a section taken on the line 2—2 of FIG. 1A;

FIG. 3 is a section of the reservoir, taken on the line 3—3 of FIG. 1A;

FIG. 4 is a section of the reservoir showing the piston rod turned to lock the rod and piston in the fully discharged position;

FIG. 5 is a section of the assembly taken on the line 5—5 of FIG. 1B;

FIG. 6 is a section through the aspiration chamber taken on the line 6—6 of FIG. 1B;

FIG. 7 is a bottom plan view of the resilient portion of the aspiration chamber housing;

FIG. 8 is a side view of the resilient portion of the aspiration chamber housing;

FIG. 9 shows a modification wherein the intermediate tubing has a spiraled section; and FIG. 10 is a modification wherein the intermediate tubing is of the same diameter throughout and straight.

FIG. 11 shows a top plan view of a modification utilizing a modified receiver arrangement;

FIG. 12 is a section view taken on the line 12—12 of FIG. 11;

FIG. 13 is a section view taken on the line 13—13 of FIG. 12, also showing a blunt needle above the modified aspiration assembly;

FIG. 14 is a side elevation of the two-part resilient plug of the modified aspiration assembly;

FIG. 15 is a bottom plan view of the plug as shown in FIG. 14;

FIG. 16 is an exploded section view of the two-part resilient plug;

FIG. 17 is a top plan view of a modification of an aspiration assembly and a modification of a resilient plug, showing a cylindrical perforation or orifice extending through the plug, rather than a slit;

FIG. 18 is a section on the aspiration assembly and plug taken on the line 18—18 of FIG. 17;

FIG. 19 is a section taken on the line 19—19 of FIG. 18;

FIG. 20 is an exploded sectional view the aspiration assembly, plug and retention ring;

FIG. 21 is a section taken on the line 21—21 of FIG. 20;

FIG. 22 is a top plan view of the aspiration assembly with the resilient plug and retainer ring removed;

FIG. 23 is a side view of the blunt needle apparatus shown attached to a syringe depicted in dashed lines;

FIG. 24 is a section of the blunt needle apparatus taken on the line 24—24 of FIG. 23;

FIG. 25 is an isometric view of the blunt needle apparatus;

FIG. 26 is a view of the distal end of the blunt needle apparatus showing more clearly the curvature at the needle tip;

FIG. 27 is a section of the needle tip taken on the line 27—27 of FIG. 26.

FIG. 28 is an elevation of a modification of the blunt needle, having a flat ended tip; and FIG. 29 is a section taken on the line 29—29 of FIG. 28.

FIG. 30 is an elevation showing a modified capacitance chamber;

FIG. 31 is a longitudinal section of the capacitance chamber shown in FIG. 30; and FIG. 32 is a section of the capacitance chamber taken on the line 32—32 of FIG. 30.

DETAILED DESCRIPTION OF PREFERRED EMBODIMENT

The blood aspiration assembly 20 has generally a proximal end 22 shown in FIG. 1A and a distal end shown generally as 24 in FIG. 1B. This description will work from the proximal end 22 toward the distal end 24. A high fluid pressure source shown schematically as 26 can comprise a fluid-filled container which is elevated, or which is surrounded by a source of increased pressure, for example, a pressure bag. Source 26 can have intravenous fluid therein. The pressure source 26 is in liquid flow connection with proximal flexible tubing section 28. Tubing 28 has its distal end connected by means known in the art to a coupling 30 for a trigger squeeze valve mechanism 32. The proximal tubing has another section 36 with its proximal end in liquid flow connection by known means to the distal end of trigger valve mechanism 32.

The distal end 38 of proximal tube section 36 is telescopically received within the port sleeve 40 of a housing 42 for a two-way valve 44. Valve housing 42 has a port sleeve 46 which telescopically receives the cylindrical end 48 of a flexible intermediate tube 50. Valve housing 42 further has a port sleeve 52 which is connected to a reservoir to be described.

The valve 44 has an interior body 54 having T-shaped flow channels 56, as known in the art, extending therethrough. Body 54 is rotatable by a handle 57. FIG. 1A shows valve body 54 positioned for liquid flow between ports 46 and 52, with flow from those ports to proximal port 40 being blocked. Handle 57 can rotate body 54 to connect ports 40 and 46 for liquid flow therebetween, and block flow from those ports to port 52. In the preferred embodiment, rotation of handle 57 is limited to ninety degrees so that port 40 cannot be connected to port 52. Rotation of handle 57 only 45° will block liquid flow between all three ports.

Port sleeve 52 telescopically receives and holds as by adhesive the cylindrical distal end 58 of a housing 60 of a reservoir 61. The housing 60 further comprises a frusto conical section 62 connected to distal end 58 and to a larger cylindrical section 64. The proximal end of section 64 has an outwardly jogging annular flange 66. Distal thereto is an annular rib 68 with an annular slot formed therebetween which receives the annular distal end 70 of an accordion pleated boot 72. Boot 72 can be of a flexible plastic with a plurality of pleated sections, as shown. At the proximal end of cylindrical section 64, a plastic disc 74 is mounted to telescopically fit within the slot formed interior of annular flange 66 and held as by adhesive. Disc 74 has a central cylindrical bore 76 having a pair of oppositely extending slots 78. Housing 60, disc 74 and valve housing 42 can be transparent plastic.

A plunger assembly 82 comprises a frustum-shaped piston 84 of plastic with slanted wall 85. Piston 84 is connected to a rod 86 which extends proximally into a ring handle 88. Part of rod 86 has a pair of oppositely extending linear lock flanges 90. Rod 86 and flanges 90 are sized to be snugly telescopically received through the conforming bore 76 and slots 78 in disc 74. Between ring 88 and flanges 90, rod 86 has an annular groove that receives and holds as by adhesive the annular proximal boot end 94.

The piston 84 is sized so that its outer extremeties are snugly and telescopically fitted against the interior of housing section 64. Piston 84 maintains a tight seal against section 64 to thus prevent liquid from passing from the distal to the proximal side of piston 84 during piston 84 compression.

Piston wall 85 conforms with the shape of reservoir housing wall 62 to be pressed snugly thereagainst when rod 86 is in the full discharge position. When piston 84 reaches this position, the proximal ends of lock flanges 90 extend just beyond the distal side of disc 74. To lock in this position handle 88 can then rotate rod 86 ninety degrees. Next, handle 88 is released. The proximal ends of flanges 90, having been rotated ninety degrees, press against the distal side of stop disc 74 to hold piston 84 locked in a discharge position (FIG. 4).

To move the piston 84 from this position to lock in the fully withdrawn position, the handle 88 can be rotated to align flanges 90 with slots 78. The handle 88 can be pulled proximally to move the distal ends of flanges 90 just beyond the proximal side of stop disc 74. Handle 88 is then rotated ninety degrees and released so that flanges 90 both extend perpendicular to the slots 78. The distal ends of flanges 90 abut the proximal side of stop disc 74 to lock rod 86 and piston 84 against distal movement.

Returning to intermediate tube 50, from its proximal end 48, tube 50 tapers at 96 into an enlarged section 98 which thence tapers at 100 (FIG. 1B) toward a smaller part 102. Part 102 extends into a distal tube end 104.

A blood aspirator receiver means 106 comprises a housing 108. Housing 108 includes a main liquid flow path or chamber 110. Housing 108 has a casing 111 which comprises a cylindrical sleeve 112 having an internal cylindrical bore 114. Bore 114 telescopically and snugly receives and holds tube end 104 as by adhesive. Bore 114 extends into and intersects a smaller central bore 116 which is part of chamber 110. Bore 116 extends distally to intersect with a larger bore 118 located within a distal sleeve 120 that is part of casing 111. Bore 118 telescopically receives and snugly holds as by adhesive the proximal end 122 of a flexible distal tube 125. As seen in FIGS. 5 and 6, the bottom of casing 111 located between sleeves 112 and 120 is rounded at 126 to provide additional strength.

Casing 111 has an externally threaded cylindrical extension 128 which is integral with sleeves 112 and 120. Extension 128 has an elliptical frustum-shaped bore 134. Bore 134 can be filled with a resilient material such as silicone rubber or the like to form a plug 136. Plug 136 is shown isolated in FIGS. 7 and 8. Plug 136 has a cylindrical arcuate bottom 138 of the same curvature as housing bore 116, as seen specifically in FIG. 6. As a result, liquid such as blood or dextrose solution, will flow smoothly through the portion of flow path or chamber 110 which is adjacent the juncture of plug bottom 138 with bore 116. This prevents any liquid such as dextrose solution or other initial resident fluid within housing 108 from accumulating within the flow path or chamber 110 when resident fluid is being withdrawn from aspirator receiver means 106.

The resilient plug 136 can be molded with the more rigid plastic casing 111 so that the plug 136 securely bonds to the bore 134. Alternatively, the plug 136 can be molded separately and installed in bore 134. In this case the truncated plug bottom 138 is of slightly greater diameter than the diameter of the apex of bore 134. The plug 136 must hence be slightly compressed to fill bore 134 when it is inserted therein.

The lateral expansion forces induced by accommodation of the additional volume of any needle inserted into plug 136 will be met by additional elastic compression of the resilient material, since the diameter of plug 136 cannot be increased due to the limitations of the surrounding bore 134. The resilient plug 136 can tightly seal the perforation produced by a needle through elastic reexpansion of the plug material after needle withdrawal.

The aspirator receiver means 106 further has a cap 142. Cap 142 has (FIG. 6) a depending internally threaded sleeve 144 to screw about extension 128. The inside surface 146 of cap top wall 148 screws flush against the flat top of extension 128 and the flat top 150 of plug 136. Cap wall 148 has a central funnel-shaped bore 151.

As seen in FIG. 5, the internal diameter of both tube ends 104 and 122 (not shown) is of the same internal diameter as housing bore 116 to likewise provide streamlined flow between tube ends 104 and 122 and bore 116. This prevents any buildup of dextrose solution or other resident fluid to avoid such buildup diluting any blood sample withdrawn from chamber 110, and also prevents buildup of blood when resident liquid reenters the housing 108 as will be described.

As seen in FIG. 1B, a plastic clamp 154 of the type commonly known in the art has openings at its proximal and distal ends to receive tube section 102. A lever arm 156 can be moved to have its end locked by catch 158 so that the tube 102 is clamped closed by the pincher points at 160 and 162.

Distal tube 125 extends distally to a female catheter connector fitting 170, as known in the art. The fitting 170 receives a catheter connector sleeve 172 which is connected to a catheter 174 as known in the art.

FIG. 9 shows a modification of the intermediate tube. The modified tube 50' has a spiralled or coiled tubing section 180 as opposed to the enlarged section 98 shown in FIGS. 1A and 1B. With either the FIG. 9 or FIGS. 1A and 1B version, the overall length of the intermediate tube is shorter than it would be if the intermediate tube had a uniform diameter such as that of the distal tube end 104, as pictured as 50" in FIG. 10.

In operation, catheter 174 is indwelling and clamp 154 is open as shown in FIG. 1B. Piston 84 of reservoir 61 is in the maximum discharge position with its wall 85 abutting the interior of housing wall 62. The plunger rod 86 has its lock flanges 90 at a ninety degree angle with the slot 78 in stop disc 74, as shown in FIG. 4.

Valve 44 is positioned to connect port 40 to port 46. From this positioning, the intravenous fluid from the high fluid pressure source 26 has filled the tubing 28, the conduit in trigger 32, the tubing 36, the port sleeves 40 and 46, intermediate tubing 50, chamber 110, distal tubing 125, fitting 170, connector 172 and catheter 174.

With the valve 44 so positioned, the pressure within the blood vessel can be monitored, or fluid administered, depending on the function of the device, or devices, connected proximally to the tubing 28.

Valve 44 is then positioned to connect reservoir port 52 to distal port 46. In so doing, port 40 and hence source 26 are blocked from connection with ports 46 and 52.

Now the assembly 20 can be operated to withdraw blood from the patient for sampling. Plunger handle 88 rotates ninety degrees to align lock flanges 90 with disc slots 78. The handle is moved proximally until the distal ends of flanges 90 pass beyond disc 74. Handle 88 and rod 86 are rotated ninety degrees to lock rod 86 in this fully withdrawn position as aforesaid. In this position, the proximal flat end of piston 84 is adjacent the distal side of disc 74.

With the piston 84 so withdrawn, a volume X of resident intravenous fluid is drawn within the reservoir housing 60 from the port sleeves 52 and 46, and intermediate tube 50. As such withdrawal occurs, the resident fluid within catheter 174, connector 172 and fitting 170, distal tube 125 and chamber 110 moves into the intermediate tube 50.

Further as such withdrawal occurs, blood flows through catheter 174 into intermediate tube 50. The sum of the internal potential liquid volumes of catheter 174, connector 172 and fitting 170, distal tube 125, chamber 110, and intermediate tube 50, is equal to a volume of Y. The volume Y is greater than the sum of the liquid volumes of the distal segment of undiluted blood and the intermediate segment of blood-resident fluid admixture which are formed within assembly 20 by the flow of the volume X of blood into assembly 20 through catheter 174 as a result of withdrawing volume X of resident fluid into reservoir housing 60. This predesignated volume relationship allows for proximal end 48 of intermediate tube 50 to contain essentially only resident fluid after the volume X of resident fluid has been withdrawn into the reservoir housing 60 from the intermediate tube 50, so that blood does not enter the reservoir housing 60 during such withdrawal.

For purposes of illustration, the volume X which can be withdrawn into reservoir housing 60 is equal to the internal liquid volume of the flow channels distal to a point shown as X in FIGS. 1A, 9 and 10. After such withdrawal is complete, the flow channel within intermediate tube 50 contains a mixture of blood and resident fluid at the point shown as X. Distal to this point the blood-resident fluid mixture progressively merges with essentially undiluted blood such that only substantially undiluted blood is contained within the flow channels distal to the clamp pinch points 160 and 162. Proximal to the point marked X, the blood-resident fluid mixture progressively merges with resident fluid which contains substantially no blood such that only resident fluid is contained within the flow channel at proximal end 48 of intermediate tube 50. Therefore, with such withdrawal, blood replaces substantially all resident fluid within chamber 110 but does not enter reservoir housing 60.

Hence, after reservoir housing 60 is filled with fluid and clamp 154 closed, the blood aspiration chamber 110 and all tubing distal to the clamp pinch points 160 and 162 are filled with essentially undiluted blood which is virtually free of resident fluid and isolated from the proximal tubing system. The volume X is predetermined by design to allow adequate clearing of substantially all of the resident fluid from the blood aspiration chamber 110 and all tubing distal to the clamp pinch points 160 and 162 and volume Y is predetermined by design to prevent blood from entering the reservoir 61.

With the blood now in the aspiration chamber 110, aspiration of the blood for sampling can be conducted. Clamp 154 is moved to the closed position with lever 156 held by catch 158 so that pinch points 160 and 162 press firmly against intermediate tube section 100 to block flow therein from one side of the points 160 and 162 to the other.

A needle 185 (FIG. 1B) of a typical needle syringe (not shown) or vacuum filled container (not shown) is moved through the funnel cap bore 151 to pass through plug 136 so that the needle point is inserted within the chamber 110. The syringe or vacuum filled container (not shown) aspirates as known in the art so that blood is aspirated from chamber 110 through needle 185 into the syringe or container (not shown). With this sample being taken, needle 185 is withdrawn from plug 136 and the sample of blood taken for proper analysis. Upon withdrawal of needle 185, the elastic material of plug 136 seals the needle perforation.

The withdrawn blood is replaced by additional blood from the patient flowing into catheter 174 toward chamber 110, since the clamp 154 has blocked off any liquid flow proximal of pinch points 160 and 162.

Following the taking of the blood sample and removal of needle 185, the clamp 154 can then be moved to the open position of FIG. 1B. Plunger handle 88 is rotated, moved to and locked in the fully discharged position with wall 85 abutting housing wall 62. This displaces the intravenous fluid from housing 60 back into the intermediate tube 50, chamber 110 and all tubing and connections distal thereto, thereby effectively clearing much of the residual blood from those flow paths. The two-way valve 44 is then rotated to connect ports 46 and 40 and block flow to and from reservoir port 52.

Any additional residual blood in the tubing and chamber 110 can be cleared by additional irrigation from the high fluid pressure source 26.

Cap 142 helps maintain plug 136 in the position shown, by counteracting any internal pressure in chamber 110 greater than atmospheric pressure, and resisting any tendency of the plug 136 to move with withdrawal of needle 185. The sloping surface of cap funnel bore 148 helps direct the needle 185 into the plug 136.

When the piston 84 is locked in the fully withdrawn position as aforesaid, such locking and holding of the reservoir 61 volume fixed will prevent flow of liquid from the second conduit toward the aspirator chamber 110 even when the clamp 154 is not employed. Hence, the locking of the piston 84 in such position is a means to inhibit flow of liquid in the second conduit toward the chamber 110 during aspiration through needle 185.

FIGS. 11-16 show a modified aspiration assembly 202 for use with a blunt needle apparatus to be described. Assembly 202 shows a modified housing 108' with a modified casing 111'. Casing 111' has cylindrical sleeves 112' and 120' which receives tube ends 104 and 122, respectively, in the manner heretofore described.

Casing 111' likewise has an upright externally threaded extension 128', with an elliptical frustum-shaped bore, like bore 134 heretofore described, which is filled with a plug 136'. Plug 136' is comprised of an upper part 208 and a lower part 210. As seen in FIG. 15, the top of upper part 208 has an arcuate recess 212, while the bottom has a projecting ridge 214.

Bottom plug part 210 has an upper recess 216 shaped to snugly receive the ridge 214. The bottom surface of plug part 208 is held to the top of plug part 210, so that the two fit together, as seen in FIGS. 12 and 13, when they are within the extension 128'. A slit 218a extends through plug part 208 from the top recess 212 through the bottom ridge 214. The slit 218a is in longitudinal alignment with the sleeve 112' of casing 111'. Lower plug part 210 likewise has a slit 218b aligned with slit 218a, to form a continuous slit through the plug 136'.

Upper plug part 208 is comprised of a more compliant material than lower part 210, although both materials can be of silicone rubber, for example. Cap 142 fits on extension 128' as heretofore described. The cap bore 151 has its bottom opening aligned with slit 218a.

FIGS. 17–22 show another modification of the aspiration assembly 220, with a resilient plug having an orifice or perforation extending therethrough, and having a different flow path. Assembly 220 has a modified housing 108" with a modified casing 111". Casing 111" has cylindrical sleeves 112" and 120" which receive tube ends 104 and 122, respectively, as by adhesive. It is noted that the views of the aspiration assembly of FIGS. 17–21 are reversed from that in FIGS. 1B and 11 & 12. The casing 111" has a modified chamber 110". The lower part of casing 111" has a raised hump 221 having a raised floor 222 with slanted sides 223. A hollow 233 extends longitudinally through hump 221, as shown in FIG. 19, to divide the hump into two opposing ridges 234.

As seen in FIGS. 18 and 22, the upper side edges 235 of the ridges 234 are curved upwardly and outwardly. The plug or septum 136" has a lower conical recess 237. Recess 237 is shaped to conform to the shape of ridges 234, so that a conduit is provided by the hollow 233 and the part of plug recess 237 extending about hollow 233. Because of the aforementioned curvature of the ridges 234, the said conduit has an enlarged central portion 238 and two smaller portions 239 in flow connection therewith.

The upper surface of plug 136" has a small central target recess 244 of a generally conical or arcuate shape. An orifice or perforation 246 extends through the axis of plug 136" to connect the center of the upper recess 244 to the center of lower plug recess 237. This perforation in a preferred embodiment is made by penetrating the plug 136" with a steel needle having an outside diameter of 1.5 mm.

The annular upper perimeter of plug 136" is recessed to receive an annular plastic retainer ring 250. Ring 250 can be held against the inner wall of extension 128" as by adhesive, to thus retain plug 136" therein.

This design is advantageous in completely displacing air from the assembly 108" when it is installed. When the saline solution is initially placed in the high fluid pressure source 26, the system is irrigated from the proximal side to the distal side of the assembly 108". This is generally done by squeezing a high pressure valve so that fluid comes from the source 26 under high pressure through tubing 28 and thence to the aspiration assembly 108". It is important to remove all the air bubbles as easily as possible.

The chamber 110" is enlarged to accommodate the blunt needle to be described. As a result, flow velocity from either of the more narrow conduit flow paths 239 into the larger central conduit portion 238 is reduced. The raised floor 222 and its slanted sides 223 create a turbulent flow path for liquid passing therethrough. This turbulence increases the probability of the flowing liquid catching air bubbles which adhere to the walls of chamber 110" and shearing the bubbles away from the walls during initial preparation of the assembly before attachment to the patient. Thus, the air bubbles are removed to avoid a possible embolism or other injury caused by injection of an air bubble into the vasculature of the patient during subsequent use of the assembly.

The needle apparatus 270 comprises a cylindrical base section 272. The proximal end of section 272 has integral exterior threads 274. Projecting laterally from opposite sides of base 272 are a pair of longitudinal gripping flanges 276. Distal to the flanges 276 is an annular stop 278. Stop 278 and flanges 276 are integral with one another and with base 272.

A blunt needle 280 has its proximal end integral with stop 278. Needle assembly 270 is thus one unitary integral and composite piece which can be molded as of plastic, such as polycarbonate, or polytetrafluoroethylene resin such as that sold under the trademark Teflon.

Referring to FIGS. 26 and 27, needle 280 has a rounded tip 284. The radius of curvature of tip 284 is about 0.25 mm, for use with the perforated plug design shown in FIGS. 18–21. With particular reference to FIG. 27, one side of the needle 280 near tip 284 is recessed at 288.

Needle apparatus base 272 has a slightly tapered longitudinal bore 290 which extends distally into a conical tapered section 292. In open communication with bore section 290 is the bore 294 of needle 280. Bore 294 tapers from a larger diameter to a smaller diameter as it extends distally. Near the distal end of needle 280, bore 294 angles at approximately 20° toward the needle side 288 and has an opening 296 through side 288. To the proximal side of opening 296, the needle 280 has a smooth slanted edge 298.

Beyond the rounded tip 284, as the needle 280 extends proximally, it can flare out into a conical section 300 having an angle of about 30°, as shown on the right side of FIG. 27. Thence the needle extends into a conical section 301 having a smaller angle than 30°, such as an angle of about 20°, also as shown on the right of FIG. 27.

As seen in viewing FIG. 23, the apparatus 270 can be attached to a syringe 325 having a neck 327 and an internally threaded annular mounting fixture 329. The exterior threads 274 of base 272 are threadingly received within connecting mount 329. This permits liquid to flow through base bore 290 into neck 329 and syringe 325.

The modified aspiration assemblies 202 and 220 are of particular use when the aspirating means is the blunt needle apparatus 270, shown in FIGS. 23–27. With respect to assembly 202, the blunt plastic needle 280 can be targeted through the cap bore 151 into the recess 212 of upper plug part 208. The arcuate shape of the recess 212 helps to guide the needle 280 toward the slit 218a. Further downward pressure on needle 280 moves it easily through slit 218a, through lower ridge 214. As the needle enters the top of lower plug part 210, the angled recess 216 helps to guide needle 280 through the lower slit 218b. The needle 280 can then pass completely through lower plug slit 218b into the bore 116' of chamber 110', as shown in FIG. 24. In this FIG. 24 position, it can be seen that the distance from the needle tip 284 to the distal side of stop 278 is less than the distance from the point where the distal side of stop 278 abuts the top of cap 142. This prevents tip 284 from striking the opposing wall of chamber bore 116'. Blood is then aspirated through opening 296 and bores 294 and 292 of needle 280 in the same fashion as previously described. Next, the needle 280 is withdrawn from slits 218b and 218a, and the blood can be taken elsewhere.

The embodiment of the plug 136" of FIGS. 18-20 can have dimensions of height of 0.5 inches (12.7 mm) from the upper surface of the plug 136" extending about recess 244, to the lower surface extending about lower plug recess 240. The diameter of the plug 136" through its largest dimension can be 0.545 inches (13.84 mm). The angle of the recess 237 can be 45°, and the diameter of the recess at its bottom can be 0.40 inches (10.16 mm) and the depth of the recess can be 0.175 inches (4.44 mm).

The recess of the plug 136" to receive the retainer ring 250 can be 0.10 inches (4.54 mm) deep and 0.075 inches (1.9 mm) wide. The upper diameter of the recess 244 can have a depth of 0.025 inches (0.63 mm) and a width of 0.125 inches (3.18 mm).

The silicone rubber for the plugs 136", can be 50 to 60 Durometer-A medical grade.

With the described plug 136" design of FIGS. 18-20, with a silicone having a hardness of about 50 to 55 Durometer-A medical grade, the depth of penetration into the plug with the polycarbonate needle 280 design as described with the force of one pound applied perpendicular to the plug 136" surface is 0.2 inches (5 mm). With a force of 2 pounds (889,600 dynes), the said needle 280 design will penetrate the said plug 0.25 inches (6.35 mm).

In contrast, using the same blunt needle, penetration of intact normal human skin of the dorsum of the hand does not occur at a force of 2 pounds (889,600 dynes). In further contrast, a sharp 20-gauge steel needle of the type conventionally used with the prior art results in the penetration of the skin of the dorsum of the hand with a force of about 0.12 pounds (53,376 dynes).

Since the force required to pass the tip of the blunt needle into the plug or septum is considerably less than the force required to penetrate the surface of normal intact human skin of the hand, accidental misdirection of such forces through the blunt needle tip against the skin will not result in penetration. Therefore, the risk of needlestick while obtaining a blood sample through the septum with the blunt needle should be virtually eliminated.

The channelling of the movement of the needle 280 through the remainder of plug 136" is effected by the perforation 246 guiding the needle 280 in the proper direction. Once the initial penetration of needle 280 occurs, there is little likelihood of misdirection of the blunt needle 280.

Further, the force to achieve penetration of the skin with the blunt needle 280 is much greater than that required to achieve skin penetration with the said sharp steel needle. Hence the chance of accidental puncture of the skin by casual inadvertent contact is much less likely to occur with the blunt needle design 280 than with the conventional sharp steel needle.

With the plug 136" of the described design for FIGS. 18-20, total penetration of the plug 136" by the polycarbonate needle 280 having dimensions heretofore described to position the tip 284 within aspiration chamber 110", as illustrated in FIG. 24 for aspiration chamber 110', can be performed by a force of 4.2 pounds (18,681,600 dynes) applied perpendicular to the plug surface.

Needles 280 having tips with a radius of curvature of 0.20 mm. to about 1 mm can also be used with the plug 136" with dimensions previously described. With larger plugs 136", blunt needle tips having larger radius of curvature than 1 mm, can be used, such as a radius of 2.5 mm.

FIGS. 31 and 32 show a modification of the needle 280 having a modified tip 310. The end 314 of tip 310 is flat, and in an embodiment, can have a diameter of 1.0 mm. The tip angle at 312 can be about 15° and can extend proximally into a section 313 having a smaller angle of about 10°, as seen viewing FIG. 32 toward the right side. The flat end surface 314 can have an area of 0.78 square mm. which can be of circular shape. One side of the distal end of needle 310 is recessed at 318 and has an opening 320 extending therethrough in liquid flow communication with needle bore 294'.

In contrast with the aforementioned easy penetration of the skin achieved by the typical steel needle, the needle 280 with tip 310 of FIGS. 28 & 29 fails to penetrate the skin of the dorsum of the hand when directed against it at a force of 2.3 pounds (1,023,040 dynes). Hence, it too is much less likely than the conventional steel needle to penetrate the human skin accidentally when the aspiration needle contacts the skin through casual contact.

The force required to achieve depths of penetration of 0.2 inches (5.08 mm) and 0.25 inches (6.35 mm) into the plug 136" of dimensions previously described, with the flat end needle 310 as described for FIGS. 28 & 29, is substantially the same as the forces given for the rounded end needle 280 of dimensions previously described.

Blunt needle 310 having a flat end 314 with diameters of from 0.2 mm. to about 2 mm. can also be used with the plug 136" described previously. With plugs of larger size, needles 310 with flat end 314 of up to about 5 mm. diameter can be used.

Hence, with the blunt needle of FIGS. 28 & 29, and the plug design described, the penetration force needed to obtain initial penetration of the plug is less than that required to pierce the human skin. The chance of piercing the skin by a misdirected needle is thus much less when using the blunt needle described for FIGS. 28 and 29, than when using a conventional steel needle.

This needle design of FIGS. 28 & 29 can completely penetrate the previously described plug 136" into the aspiration chamber 110" at a perpendicular application force of 5 pounds (2,224,000 dynes).

The needle designs of FIGS. 25-27, and of FIGS. 28 & 29 having solid tips are more preferable than a tip with a longitudinal bore extending directly through it. The FIG. 25-27, 28 and 29 designs provide greater rigidity and strength, and provide surface area at the tip which better distributes force against the skin than with a needle having a longitudinal bore extending through the axis of the tip.

For both the round end and flat end blunt needle, the effective radius of curvature of the round end, and the diameter or surface area of the flat end, can vary as the angle of the adjacent needle section varies from 30 degrees, and can also vary with plugs with silicone of different ranges of hardness to the extent that such designs allow the blunt needle tip to penetrate into the perforation at forces less than the forces required to cause the needle tip to penetrate into human skin.

FIGS. 30-32 show a modified intermediate tube section 50'''. It comprises a rectangular casing 340 having upper and lower longitudinal sections 342 and 344 of strong rigid plastic held together as by adhesive (FIG. 31). At the longitudinal ends of casing 340 are a pair of bores 348 and 349 which receive cylindrical plastic insert tubes 350 and 352, respectively. Tubes 350 and 352 have raised rounded edges 355 and 357 at their outer ends.

The ends of the tubes 355 and 357 are in liquid flow communication with a serpentine coil 359 which extends through casing 340. The cross section of coil 359 is of oblong or elliptical shape as seen in FIG. 31. The oblong or elliptical shaped bore of the serpentine coil minimizes the top surface area needed to achieve an adequate capacitance volume. This provides for adequate volume in a compact, strong, and noncompliant structure. The noncompliance is important in order for blood pressure readings to be made or monitored with a transducer in fluid connection with the invention.

As known in the art, the trigger squeeze 32 can be operated to cause fluid flow from fluid source 26 into the assembly flow paths distal of trigger squeeze 32.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. In a fluid-filled extra-corporeal blood aspiration system for sampling pressurized blood from the human body, the system being for connection with a catheter having a bore in fluid connection with a pressurized blood vessel, the system having means for elevating the fluid pressure above the pressure within said blood vessel so that fluid flows from the system into the blood vessel and the system having means for reducing said fluid pressure below the pressure within said blood vessel so that blood flows from said blood vessel into said system, improvements comprising:

an aspirator including an axially extending cannula having a blunt distal tip, said cannula having a bore with first and second openings adjacent opposite ends thereof, said aspirator further including a receptacle in communication with said bore through said second opening thereof;

an aspirator receiver forming part of the blood aspiration system and including a housing having a flow channel for communication with the human vasculature for flowing blood through the flow channel, said housing carrying a receiver portion, the receiver portion having an outer surface and an inner surface and an upwardly projecting cavity along said inner surface, the receiver portion being penetrable by said cannula to locate the first opening of said cannula in communication with said flow channel and enable blood flow from said flow channel through said first opening, said bore and said second opening into said receptacle, said flow channel ramping upwardly into said upwardly projecting cavity, said upwardly projecting cavity functioning to receive blood from said upward ramping flow channel;

said aspirator receiver portion being preperforated to form a receiver channel for receiving the cannula upon penetration thereof by said cannula, said housing receiver portion being formed of a resilient material whereby said receiver channel is normally closed.

2. Apparatus according to claim 1 wherein said receiver channel extends between said inner and outer surfaces and normally sealing said housing receiver portion between said flow channel and ambient atmosphere so that blood flowing through said flow channel is in direct contact with said receiver channel.

3. Apparatus according to claim 2 wherein the flow channel has opposite ends and further having first and second flow passageways in communication with the flow channel at its opposite ends, said second flow passageway being in fluid communication with said means for reducing fluid pressure, said flow channel being larger in cross sectional area than the cross-sectional area of either of said flow passageways, said inner surface of said housing portion lying in juxtaposition to said flow channel and said receiver channel.

4. Apparatus according to claim 1 wherein a central recess is defined in said outer surface adjacent said receiver channel for initially receiving the distal tip of said cannula and locating said cannula for penetration through said preperforation in said housing portion and disposition of said first opening of said cannula in communication with said flow channel.

5. Apparatus according to claim 4 wherein said flow channel is generally cylindrical in shape, the inner surface of said housing portion forming part of said flow channel having an arcuate segment forming a portion of the generally cylindrical shape of said flow channel.

6. Apparatus according to claim 1 wherein said housing has a generally arcuate flow channel and said housing portion has an inner surface, the inner surface of said housing portion forming part of said flow channel and being formed arcuately to generally conform to the arcuate shape of said flow channel.

7. Apparatus according to claim 1 wherein said housing includes an opening in communication with said flow channel and a septum in said opening normally occluding said opening.

8. Apparatus according to claim 7 wherein the flow channel has opposite ends, said housing having flow passageways in communication with the flow channel at its opposite ends, said flow channel being larger in cross sectional area than the cross-sectional area of either of said flow passageways, said septum lying in juxtaposition to said flow channel and having inner and outer surfaces interfacing with the flow channel and ambient atmosphere, respectively, and said ramping induces turbulent flow in said flow channel adjacent said inner surface of said septum.

9. Apparatus according to claim 1 wherein the flow channel has opposite ends, said housing having flow passageways in communication with the flow channel at its opposite ends, said flow channel being larger in cross sectional area than the cross-sectional area of either of said flow passageways.

10. Apparatus according to claim 9 wherein said housing portion lies in juxtaposition to said flow channel, and means forming part of said housing for inducing turbulent flow in said flow channel.

11. Apparatus according to claim 9 wherein said flow channel extends generally in a first direction, said housing portion having inner and outer surfaces interfacing the flow channel and ambient atmosphere, respectively, said receiver channel extending generally in a second direction between said inner and outer surfaces and generally perpendicular to said first direction, said receiver channel normally sealing between said flow channel and ambient atmosphere, said cannula having an axis extending generally in said second direction upon penetration of said housing portion by said cannula, means cooperable between said cannula and said aspiration receiver for limiting the extent of penetration of said cannula through said receiver channel, said receiver channel having a length in said second direction correlated with said limiting means and the length of said cannula such that said first opening lies in said flow channel when said limiting means limits the extent of penetration of said cannula through said receiver channel.

12. Apparatus according to claim 1 wherein said housing portion has inner and outer surfaces, and means for enabling penetration of said resilient material by said cannula with less force adjacent said outer surface than adjacent said inner surface.

13. Apparatus according to claim 12 wherein said enabling means includes a housing portion having a greater lateral extent adjacent said outer surface than its lateral extent adjacent said inner surface, said receiver channel extending between said inner and outer surfaces and normally sealing said housing portion between said flow channel and ambient atmosphere.

14. Apparatus according to claim 12 wherein said penetration means comprises first and second different materials forming two discrete housing portion parts adjacent said outer and inner surfaces, respectively, of said housing portion, said first housing portion part being formed of a material having a greater compliance than the compliance of the material forming said second housing portion part.

15. Apparatus for use with a blood aspiration system for sampling blood from the human body, comprising:
an aspirator including an axially extending cannula having a distal tip, said cannula having a bore with first and second openings adjacent opposite ends thereof, said aspirator further including a receptacle in communication with said bore through said second opening thereof;
an aspiration receiver forming part of the blood aspiration system and including a housing having a flow channel for communication with the human vasculature for flowing blood through the flow channel, said housing having a portion penetrable by said cannula to locate the first opening of said cannula in communication with said flow channel and enable blood flow from said flow channel through said first opening, said bore and said second opening into said receptacle, said portion of said housing having an inner surface and an outer surface interfacing with the flow channel and ambient atmosphere, respectively, a portion of said inner surface having a concave recess portion, a bottom wall of said housing having a convex hump portion, said hump portion being complementarily shaped to said recess portion to matingly engage the same, said hump portion having a longitudinal cutout defined therein which has an upwardly inclined portion and a downwardly inclined portion and which defines a portion of said flow channel; said housing portion forming an opening upon penetration of said housing portion by said cannula for receiving said cannula, said housing portion being formed of a resilient material for sealing said opening upon withdrawal of said cannula from said housing portion.

16. Apparatus according to claim 15 wherein the flow channel has opposite ends, said housing having flow passageways in communication with the flow channel at its opposite ends, said flow channel being larger in cross sectional area than the cross-sectional area of either of said flow passageways, said inner surface of said housing portion lying in juxtaposition to said flow channel.

17. Apparatus according to claim 15 wherein a central recess is defined in said outer surface for initially locating said cannula tip for penetration through said housing portion and disposition of said first opening of said cannula in communication with said flow channel.

18. Apparatus according to claim 17 wherein said flow channel is generally cylindrical in shape, the inner surface of said housing portion forming part of said flow channel having an arcuate segment forming a portion of the generally cylindrical shape of said flow channel 19. Apparatus according to claim 15 wherein said housing has a generally arcuate flow channel and said housing portion has an inner surface, the inner surface of said housing portion forming part of said flow channel and being formed arcuately to generally conform to the arcuate shape of said flow channel.

20. Apparatus according to claim 15 wherein said housing includes an opening in communication with said flow channel and a septum in said opening normally occluding said opening.

21. Apparatus according to claim 20 wherein the flow channel has opposite ends, said housing having flow passageways in communication with the flow channel at its opposite ends, said flow channel being larger in cross sectional area than the cross-sectional area of either of said flow passageways, said septum lying in juxtaposition to said flow channel and defining said inner and outer surfaces interfacing with the flow channel and ambient atmosphere, and wherein said portion of said flow channel defined by said recess portion and by said cutout in said hump portion induces turbulent flow in said flow channel adjacent said inner surface of said septum.

22. Apparatus according to claim 15 wherein said flow channel extends generally in a first direction, said cannula having an axis extending generally in a second direction generally perpendicular to said first direction upon penetration of said housing portion by said cannula, means cooperable between said cannula and said aspiration receiver for limiting the extent of penetration of said cannula through said housing portion, said inner and outer surfaces having a distance therebetween in said second direction correlated with said limiting means and the length of said cannula such that said first opening lies in said flow channel when said limiting means limits the extent of penetration of said cannula through said housing portion.

23. Apparatus according to claim 15 wherein said housing portion has means for enabling penetration of said resilient material by said cannula with less force adjacent said outer surface than adjacent said inner surface.

24. Apparatus according to claim 23 wherein said enabling means includes a housing portion having a greater lateral extent adjacent said outer surface than its lateral extent adjacent said inner surface.

25. Apparatus according to claim 23 wherein said penetration means comprises first and second different materials forming two discrete housing portion parts adjacent said outer and inner surfaces, respectively, of said housing portion, said first housing portion part being formed of a material having a greater compliance than the compliance of the material forming said second housing portion part.

26. Apparatus for use with a blood aspiration system for sampling blood from the human body, comprising:
   an aspirator including an axially extending cannula having a distal tip, said cannula having a bore with first and second openings adjacent opposite ends thereof, said aspirator further including a receptacle in communication with said bore through said second opening thereof; and
   an aspiration receiver forming part of the blood aspiration system and including a housing having a flow channel for communication with the human vasculature for flowing blood through the flow channel, said housing having a septum penetrable by said cannula to locate the first opening of said cannula in communication with said flow channel and enable blood flow from said flow channel through said first opening, said bore and said second opening into said receptacle;
   said septum forming an opening upon penetration of said septum by said cannula, said septum being formed of a resilient material for sealing said opening upon withdrawal of said cannula from said housing portion;
   said septum having an inner surface and an outer surface interfacing with the flow channel and ambient atmosphere, respectively, a portion of said inner surface having a concave recess portion, a bottom wall of said housing having a convex hump portion, said hump portion being complementarily shaped to said recess portion to matingly engage the same, a longitudinal cutout being defined in said hump portion, said cutout having an upwardly inclined portion and a downwardly inclined portion and defining a portion of said flow channel which induces turbulent flow.

27. Apparatus according to claim 26 wherein the flow channel has opposite ends, said housing having flow passageways in communication with the flow channel at its opposite ends, said flow channel being larger in cross sectional area than the cross-sectional area of either of said flow passageways.

28. Apparatus according to claim 26 wherein said septum has a central recess in said outer surface for initially receiving the distal tip of said cannula and locating said cannula for penetration through said septum and disposition of said first opening of said cannula in communication with said flow channel.

29. Apparatus according to claim 28 wherein said flow channel is generally cylindrical in shape, the inner surface of said septum forming part of said flow channel having an arcuate segment forming a portion of the generally cylindrical shape of said flow channel.

30. Apparatus according to claim 26 wherein said housing has a generally arcuate flow channel and, the inner surface of said septum forming part of said flow channel and being formed arcuately to generally conform to the arcuate shape of said flow channel.

31. Apparatus according to claim 26 wherein the flow channel has opposite ends, said housing having flow passageways in communication with the flow channel at its opposite ends, said flow channel being larger in cross sectional area than the cross-sectional area of either of said flow passageways, said septum lying in juxtaposition to said flow channel.

32. Apparatus according to claim 26 wherein said flow channel extends generally in a first direction, said cannula having an axis extending generally perpendicular to said first direction upon penetration of said septum by said cannula, means cooperable between said cannula and said aspiration receiver for limiting the extent of penetration of said cannula through said septum, said inner and outer surfaces having a distance therebetween in said second direction correlated with said limiting means and the length of said cannula such that said first opening lies in said flow channel when said limiting means limits the extent of penetration of said cannula through said septum.

33. Apparatus according to claim 26 wherein said septum has means for enabling penetration of said resilient material by said cannula with less force adjacent said outer surface than adjacent said inner surface.

34. Apparatus according to claim 33 wherein said penetration means comprises first and second different materials forming two discrete septum parts adjacent said outer and inner surfaces, respectively, of said septum, said first septum part being formed of a material having a greater compliance than the compliance of the material forming said second septum part.

35. A system as in claim 1, wherein said inner surface is a bottom surface of said receiver portion disposed in opposing relation to a bottom wall of said housing.

* * * * *